United States Patent
Fukui et al.

(10) Patent No.: US 7,312,373 B2
(45) Date of Patent: Dec. 25, 2007

(54) NONHUMAN MODEL ANIMAL LACKING THE ABILITY TO CONTROL LYMPHOCYTE MIGRATION

(75) Inventors: Yoshinori Fukui, Fukuoka (JP); Takehiko Sasazuki, Tokyo (JP)

(73) Assignee: Japan Science and Technology Agency, Kawaguchi-shi (JP)

(*) Notice: Subject to any disclaimer, the term of this patent is extended or adjusted under 35 U.S.C. 154(b) by 137 days.

(21) Appl. No.: 10/886,364

(22) Filed: Jul. 7, 2004

(65) Prior Publication Data

US 2005/0071894 A1    Mar. 31, 2005

Related U.S. Application Data

(63) Continuation-in-part of application No. PCT/JP02/08372, filed on Aug. 20, 2002.

(30) Foreign Application Priority Data

Jan. 7, 2002    (JP)    ............... 2002-000707

(51) Int. Cl.
    A01K 67/027    (2006.01)
(52) U.S. Cl. .......................... 800/18; 800/14
(58) Field of Classification Search .................. 800/3, 800/8, 14, 21, 18
    See application file for complete search history.

(56) References Cited

OTHER PUBLICATIONS

Mullins LJ, Mullins JJ. Transgenesis in the rat and larger mammals. J Clin Invest. 1996 ;97(7):1557-60.*
Moreadith RW, Radford NB. Gene targeting in embryonic stem cells: the new physiology and metabolism. J Mol Med. 1997;75(3):208-16.*
Campbell KHS and Wilmut I. Totipotency or multipotentiality of cultured cells:Applications and progress Theriogenology 1997, 47:63-72.*
Houdebine LM. Production of pharmaceutical proteins from transgenic animals. J Biotechnol. 1994;34(3):269-87.*
Holschneider DP and Shih JC. Genotype to phenotype: challenges and opportunities. Int. J. Devl Neuroscience 2000, 18:615-618.*
Taurog JD, Lowen L, Forman J, Hammer RE. HLA-B27 in inbred and non-inbred transgenic mice. Cell surface expression and recognition as an alloantigen in the absence of human beta 2-microglobulin. J Immunol. 1988 ;141(11):4020-3.*
Mullins JJ, Sigmund CD, Kane-Haas C, Gross KW, McGowan RA. Expression of the DBA/2J Ren-2 gene in the adrenal gland of transgenic mice. EMBO J. 1989;8(13);4065-72.*
Hochepied T, Schoonjans L, Staelens J, Kreemers V, Danloy S, Puimege L et al Breaking the species barrier: derivation of germline-competent embryonic stem cells from Mus spretus x C57BL/6 hybrids. Stem Cells. 2004; 22(4):441-447.*
Mullins JJ, Peters J, Ganten D. Fulminant hypertension in transgenic rats harboring the mouse Ren-2 gene.Nature. 1990;344(6266):541-4.*
Hammer RE, Maika SD, Richardson JA, Tang JP, Taurog JD. Spontaneous inflammatory disease in transgenic rats expressing HLA-B27 and human beta 2m: an animal model of HLA-B27-associated human disorders. Cell. 1990;63(5):1099-112.*
Yoshinori Fukui, et al., Haematopoietic CellSpecific CDM Family Protein DOCK2 Is Essential For Lymphocyte Migration, Nature, vol. 412, Aug. 2001, p. 826-831.
Douglas A. Lauffenburger, et al., Cell Migration: A Phsically Integrated Molecular Process,Cell, vol. 84, Feb. 1996, p. 359-369.
Hiroshi Nishihara, et al., DOCK2 Mediates T Cell ReceptorInduced Activation Of RAC2 and IL-2 Transcription, Biochemical And Biophysical Research Communications, 296, (2002) p. 716-720.
Hiroshi Nishihara, et al., Non-Adherent Cell-Specific Expression Of DOCK2, A Member Of The Human CDMFamily Proteins, Biochimica et Biophysica Acta 1452 (1999) p. 179-187.
Karin Reif, et al., The CDM Protein DOCK2 In Lymphocyte Migation, Trends In Cell Biology, vol. 12, No. 8, Aug. 2002, p. 368373.
Norbert Wagner, et al., L-Selectin And β Integrin Synergistically Mediate Lymphocyte Migration To Mesenteric Lymph Nodes, Eur. J. Immunol., vol. 28 (1998) p. 3832-3839.

* cited by examiner

*Primary Examiner*—Anne-Marie Falk
*Assistant Examiner*—Anoop K. Singh
(74) *Attorney, Agent, or Firm*—Frommer Lawrence & Haug LLP; Thomas J. Kowalski; Deborah L. Lu

(57) ABSTRACT

The present invention provides a animal model useful in identifying a molecule controlling in a lymphocyte-specific manner migration and thus elucidating immune-related diseases and pathogenic conditions such as allergy, autoimmune diseases, GvH and graft rejections at a molecular level, or in developing a novel therapy. A nonhuman animal model such as a DOCK2 knockout mouse, in which the function to control lymphocyte migration has been deleted or suppressed, is generated by deleting DOCK2 gene on the chromosome. In this DOCK2 knockout mouse, the function of activating Rac to mediate actin cyteskeleton, the lymphocyte migration function in response to stimuli with chemokines such as SLC, SDF-1, BLC, the homing function to secondary lymphoid organs such as spleen, lymph nodes and Peyer's patches, and the function of emigrating mature thymic T cells into peripheral blood in response to stimulus with chemokine ELC are impaired, and as a result of this, immune responses are suppressed.

9 Claims, 5 Drawing Sheets

NONHUMAN MODEL ANIMAL LACKING THE ABILITY TO CONTROL LYMPHOCYTE MIGRATION

REFERENCE TO RELATED APPLICATIONS

This application is a continuation-in-part of International Patent Application PCT/JP02/08372 filed Aug. 20, 2002, which claims priority from Japanese Patent Application JP 2002-707 filed Jan. 7, 2002. Each of these applications, and each application and patent mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference.

Furthermore, all documents cited in this text, and all documents cited or referenced in documents cited in this text, and any manufacturer's instructions or catalogues for any products cited or mentioned in this text, are hereby incorporated herein by reference.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. patent law; namely, that these terms are closed ended.

TECHNICAL FIELD

The present invention relates to a nonhuman animal model lacking the function to control lymphocyte migration whose function to control lymphocyte migration is lacked or suppressed by deleting DOCK2 gene, a haematopoietic cell-specific CDM family protein, on the chromosome, a method for screening promoters or suppressors of the function to control lymphocyte migration with the use of the model nonhuman animal, a protein controlling lymphocyte migration which promotes reorganization of cytoskeleton through activating Rac, or DNA encoding the protein controlling lymphocyte migration, or the like.

BACKGROUND ART

Immune-response is an indispensable defense mechanism against infection for a living body and immune cells are continuously patrolling within a living body in order to rapidly cope with various sources of infection. This feature of the constituting cells to move around without cease is not observed in other living complex systems and has been evolved as a unique feature to the immune system. It is known that, among immune cells, cells such as neutrophils and macrophages function at the early defense against infection whereas T and B lymphocytes induce the antigen-specific immune-response upon recognition of foreign substances through their antigen receptors. Differentiation of such T and B lymphocytes takes place in primary lymphoid organs such as thymus and bone marrows. The differentiated lymphocytes then migrate to a particular compartment in secondary lymphoid organs such as spleen, lymph nodes and Peyer's patches (lymphoid organ in the small intestine), where these lymphocytes induce specific immune-responses by recognizing, via the antigen receptors, antigens recruited from various tissues. In this process, it is considerably crucial for the establishment of immune-response that the lymphocytes migrate into a particular site in secondary lymphoid organs. Although lymphocyte migration has so far been known as being induced by proteins collectively referred to as chemokines of various kinds, the molecular mechanism controlling lymphocyte migration itself has been remained unknown.

Change in cellular polarization and reorganization of cytoskeleton is indispensable for cell migration (Cell 84, 359-369, 1996), both of which have been known to be regulated by low molecular-weight G proteins as Rho, Rac and Cdc42 (Proc. Natl. Acad. Sci. USA 92, 5027-5031, 1995; Science 279, 509-514, 1998; J. Cell Biol. 141, 1147-1157, 1998; Science 287, 1037-1040, 2000). Among these molecules, Rac yields driving force for cell mobility by forming actin-rich lamellipodial protrusion (Science 279, 509-514, 1998; Cell 103, 227-238, 2000). Meanwhile, molecules like CED5, DOCK180 and Myoblast city (MBC) that demonstrate structural homology have been identified for *Caenorhabditis elegans*, humans and *Drosophila melanogaster*, which molecules are called CDM family molecules with their acronyms and all of which are thought to be implicated in reorganization of cytoskeleton by functioning in the upstream of Rac (Mol. Cell Biol. 16, 1770-1776, 1996; J. Cell Biol. 138, 589-603, 1997; Nature 392, 501-504, 1998; Genes Dev. 12, 3331-3336, 1998; Genes Dev. 12, 3337-3342, 1998; Nature Cell Biol. 2, 131-136, 2000). Although genetic analysis using mutants has shown that the CED-5 and Myoblast City are crucial for migration of particular types of cells (J. Cell Biol. 138, 589-603, 1997; Nature 392, 501-504, 1998; Nature Cell Biol. 2, 131-136, 2000), in what physiological way the CDM family proteins function in mammals has been left unknown.

It is known than DOCK2 (KIAA0209; DNA Res. 3, 321-329) encodes other CDM family protein member specifically expressed in human haematopoietic cells and that the DOCK2 binds to Rac in 293T kidney cells for activating Rac (Biochem. Biophys. Acta 1452, 179-187, 1999). On the other hand, the present inventors have found upon isolating a novel Hch gene belonging to CDM family from the mouse thymus cDNA library, that the Hch gene product is consisted of 1828 amino acids and SH3 domain is encoded at its N-terminus (Nature, Vol 412, 23 August, 826-831, 2001). Further, it was confirmed in northern blotting using mouse tissues that Hch expression is localized only in the thymus and spleen contrary to the DOCK180 expression which is observed in various organs, and analysis using cell lines provided confirmation that Hch expression is observed in all of T and B cells and macrophages except for two variant T cell lines. Moreover, the present inventors have demonstrated that a significant change in cell morphology as well as enhancement of adhesiveness can be detected by introducing Hch into mutant T cell lines lacking Hch expression. Among the 1828 amino acids encoded by Hch, 1677 amino acids were identical with those of human DOCK2, thus Hch was thought to be mouse homologue of DOCK2, yet physiological function of the DOCK2 remained unrevealed.

Even though immune-response is an indispensable mechanism for a living body, diseases or pathogenic conditions developed as a result of emergence of immune-response, for example autoimmune diseases, graft rejections, GvH, etc., are being focused as a problem which modern medicine is expected to work out for the resolution. For elucidating these diseases or pathogenic conditions at a molecular level or for developing a new therapy for these diseases or pathogenic conditions, molecules have been wanted to be identified that specifically control lymphocyte migration. The subject of the present invention is to identify molecules controlling in a lymphocyte-specific manner migration, and to provide useful animal models for elucidating immune-related diseases or pathogenic conditions such as allergy, autoimmune diseases, GvH or graft rejections at a molecular level, or for developing a new therapy for these diseases or pathogenic conditions.

The present inventors isolated the CDM family DOCK2 (Hch) gene, which is specifically expressed in the immune-system, from a mouse thymus cDNA library, and generated the knockout mice in order to reveal the in vivo function of the gene. DOCK2 knockout mice were born at the expected mendilian ratio without apparent abnormality. However, the numbers of T and B lymphocytes in secondary lymphoid organs such as spleen and lymph nodes were considerably reduced compared to those of wild-type mice. When lymphocytes labeled with fluorescence were intravenously injected into DOCK2 knockout mice for analyzing homing to lymph nodes, homing activity of T and B lymphocytes of the knockout mice was reduced to around 1/10 compared to that of wild-type mice. On the other hand, an efficient homing of lymphocytes to lymph nodes was observed in wild-type mice. These findings thus suggest that homing to secondary lymphoid organs might be impaired in DOCK2 knockout mice owing to an intrinsic defect in lymphocytes.

To address the involvement of DOCK2 molecules in lymphocyte mobility, migration activity in response to various chemokines were compared between the knockout and wild-type mice. No difference was observed between the knockout and wild-type mice as to migration activity of macrophages to chemokines such as MCP-1 or SDF-1. However, contrary to the fact that T and B lymphocytes from wild-type mice actively migrate in response to chemokine stimuli such as with SLC, SDF-1 or BLC, migration of T and B lymphocytes from the knockout mice were significantly impaired. Upon stimulating lymphocytes of knockout mice with chemokines, Rac activation and actin polymerization were observed that peaked at 15 sec. Such responses were disappeared in the knockout mouse lymphocytes. Contrary, no difference was found between the knockout and wild-type mice as to PKB and ERK activations and calcium immigration. These observations demonstrate that DOCK2 specifically controls lymphocyte migration by mediating reorganization of cyteskeleton through activating Rac.

There was no marked abnormality in the differentiation of T and B lymphocytes in the primary lymphoid organs of DOCK2 knockout mice. Peripheral T lymphocytes from the knockout mice, however, were significantly decreased compared to that of the wild-type mice. Since chemokine ELC are known to be involved in emigration of mature thymic T cells from thymus, emigration of these T cells in response to ELC was examined by using thymus organ cultures. The results showed that the emigration efficiency of the knockout mice was reduced to about 1/20 compared to that of the wild-type mice. These results suggest that the emigration defect in mature thymic T cells is responsible for decrease in the peripheral blood T lymphocytes of the knockout mice.

Chemokines such as SLC, ELC and BLC are called "immune-chemokines" and are known to play an essential role in architecture of secondary lymphoid organs. Marked atrophy of lymphoid follicles, straying of lymphocytes into red pulp, and disappearance of marginal-zone B cells were observed in the immunohistological analysis for the spleen of DOCK2 knockout mice. Atrophy of lymphoid follicles was similarly observed in other secondary lymphoid organs such as lymph nodes and Peyer's patches. Besides, marked aberration in distribution of mature thymic T cells in the thymus of the knockout mice was found. It was thus suggested that lymphocytes of DOCK2 knockout mice did not exercise migration activity in response to stimuli with various chemokines, leading to structural abnormality in the immune system.

To study the influence of DOCK2 deficiency on immune-response, mice were immunized with E$\alpha$-derived peptide, which is known to bind to MHC class II I-A$^b$, and the antigen-specific T-cell responses were analyzed. As a result, proliferation response of T cells were observed in an antigen concentration-dependent manner in wild-type mice, whereas such T cell response was not observed in DOCK2 knockout mice. DNP-KLH was also immunized to mice to analyze the KLH-specific antibody production, and the antibody production in DOCK2 knockout mice was observed to have been significantly impaired in DOCK2 knockout mice. These findings thus suggest that primary immune-response was suppressed in DOCK2 knockout mice 7 days after the immunization.

Taking above findings together, it was demonstrated for the first time that DOCK2 is an essential molecule controlling lymphocyte mobility by mediating reorganization of cyteskeleton through activating Rac, and that DOCK2 deficiency largely affect architecture of the immune system and immune-response. These findings are expected to serve for the development of new therapy for immune-related diseases such as allergy, autoimmune diseases and graft rejections by artificially controlling lymphocyte mobility with DOCK2 as a target. The present invention has been completed based on these findings.

DISCLOSURE OF THE INVENTION

The present invention relates to a nonhuman animal model lacking the function to control lymphocyte migration wherein the function to control lymphocyte migration is lacked or suppressed by deleting DOCK2 gene on the chromosome ("1"); the nonhuman animal model lacking the function to control lymphocyte migration according to "1", wherein the function to control lymphocyte migration is a function to mediate cytoskeletal reorganization through activating Rac ("2"); the nonhuman animal model lacking the function to control lymphocyte migration according to "1", wherein the function to control lymphocyte migration is a migration function of lymphocytes in response to stimuli with chemokines such as SLC, SDF-1, BLC ("3"); the nonhuman animal model lacking the function to control lymphocyte migration according to "1", wherein the function to control lymphocyte migration is a homing function to secondary lymphoid organs such as spleen, lymph nodes and Peyer's patches ("4"); the nonhuman animal model lacking the function to control lymphocyte migration according to "1", wherein the function to control lymphocyte migration is a function to emigrate mature thymic T cells into peripheral blood in response to chemokine stimulus with ELC or a function of intra-thymus migration of CD4+CD8+ immature thymocytes in response to chemokine stimulus with SDF-1 ("5"); the nonhuman animal model lacking the function to control lymphocyte migration according to any of "1" to "5", wherein actin polymerization in response to chemokine stimulus is almost totally disappeared in lymphocytes ("6"); the nonhuman animal model lacking the function to control lymphocyte migration according to any of "1" to "6", wherein marked atrophy of lymphoid follicles, straying of lymphocytes into red pulp, and disappearance of marginal-zone B cells are observed ("7"); and the nonhuman animal model lacking the function to control lymphocyte migration according to any of "1" to "7", wherein the nonhuman animal is a mouse ("8").

The present invention also relates to a method for screening a promoter or suppressor of the function to control lymphocyte migration, wherein a test substance is administered to the nonhuman animal model lacking the function to control lymphocyte migration according to any of "1" to "8", or a test substance is brought into contact with tissues, organs or cells from said nonhuman animal model and a wild-type animal to measure/assess the change in the function to control lymphocyte migration ("9"); the method for screening a promoter or suppressor of the function to control lymphocyte migration according to "9", wherein the change in the function to control lymphocyte migration is a change in the active GTP-bound Rac ("10"); the method for screening a promoter or suppressor of the function to control lymphocyte migration according to "9", wherein the change in the function to control lymphocyte migration is a change in the migration activity of lymphocytes in response to stimuli with chemokines such as SLC, SDF-1, BLC ("11"); the method for screening a promoter or suppressor of the function to control lymphocyte migration according to "9", wherein the change in the function to control lymphocyte migration is a change in the homing activity to secondary lymphoid organs such as spleen, lymph nodes, Peyer's patches and the like ("12"); the method for screening a promoter or suppressor of the function to control lymphocyte migration according to "9", wherein the change in the function to control lymphocyte migration is a change in the number of mature T cells in peripheral blood in response to chemokine stimulus with ELC, or a change in the intrathymic migration activity of CD4+CD8+ immature thymocytes in response to chemokine stimulus with SDF-1 ("13"); the method for screening a promoter or suppressor of the function to control lymphocyte migration according to "9", wherein the change in the function to control lymphocyte migration is a change in the degree of actin polymerization in lymphocytes in response to chemokine stimuli ("14"); the method for screening a promoter or suppressor of the function to control lymphocyte migration according to "9", wherein the change in the function to control lymphocyte migration is a change in the degrees of atrophy of lymphoid follicles, straying of lymphocytes into red pulp, and disappearance of marginal-zone B cells ("15"); the method for screening a promoter or suppressor of the function to control lymphocyte migration according to any of "9" to "15", wherein the test substance is a molecule which binds to DOCK2 ("16"); the method for screening a promoter or suppressor of the function to control lymphocyte migration according to any of "9" to "16", wherein the degrees of change in the function to control lymphocyte migration of a nonhuman animal lacking DOCK2 gene on the chromosome and of a wild-type nonhuman animal are compared and assessed ("17"); the method for screening a promoter or suppressor of the function to control lymphocyte migration according to any of "9" to "17", wherein the nonhuman animal is a mouse ("18"); a promoter or suppressor of the function to control lymphocyte migration obtained by the method for screening according to any of "9" to "18" ("19"); the suppressor of the function to control lymphocyte migration according to "19", wherein said suppressor is an anti-DOCK2 antibody, a DOCK2-binding molecule or an antisense strand of DOCK2 gene ("20"); a method for screening a therapeutic agent for immune-related diseases such as allergy, antoimmune diseases, GvH, graft rejections, wherein the method for screening a promoter or suppressor of the function to control lymphocyte migration according to any of "9" to "18" is used ("21"); a therapeutic agent for immune-related diseases such as allergy, autoimmune diseases, GvH, graft rejections obtained by the screening method according to "21" ("22"); and the therapeutic agent for immune-related diseases according to "22", which is an anti-DOCK2 antibody, a DODK2-binding molecule or an antisense strand of DOCK2 gene ("23").

The present invention further relates to a protein for controlling lymphocyte migration which mediates reorganization of cytoskeleton through activating Rac ("24"); the protein for controlling lymphocyte migration according to "24", wherein said protein is DOCK2 and a DOCK2 variant ("25"); the protein for controlling lymphocyte migration according to "25", wherein DOCK2 is an expression product of Hch gene (GenBank: accession No. AYO27438) ("26"); a method using the protein according to any of "24" to "26" for controlling lymphocyte migration ("27"); DNA encoding a protein for controlling lymphocyte migration which mediates reorganization of cytoskeleton through activating Rac ("28"); DNA encoding the protein for controlling lymphocyte migration according to "28", wherein said DNA is DOCK2 gene and a DOCK2 gene variant ("29"); DNA encoding the protein for controlling lymphocyte migration according to "29", wherein DOCK2 gene is Hch gene (GenBank: accession No. AYO27438) ("30"); and a method using DNA according to any of "28" to "30" for expressing the protein for controlling lymphocyte migration ("31").

a: Total cell extracts were analyzed by immunoblotting using anti-DOCK2 polyclonal antibody. A non-specific band (NS) is shown as a loading control.

b: Total cell extracts were analyzed by incubating with (bottom panel) or without (top panel) GST-fusion PAK1 RBD using anti-Rac monoclonal antibody.

c: Cells were stained with propidium iodide (PI) or phalloidin and analyzed using a fluorescence microscope with Nomarski optics. Nomarski- and phalloidin-stained images were taken from the same cell.

d: After staining 25-7 cells with anti-HA antibody, DOCK2 (green area) and phalloidin (red area) were detected. The cell images were taken with a laser confocal microscope by scanning the cells from the top to the bottom (from 1 to 9) by a 2-μm interval. A scale bar in FIG. 1d indicates 1 μm.

Figure 2:
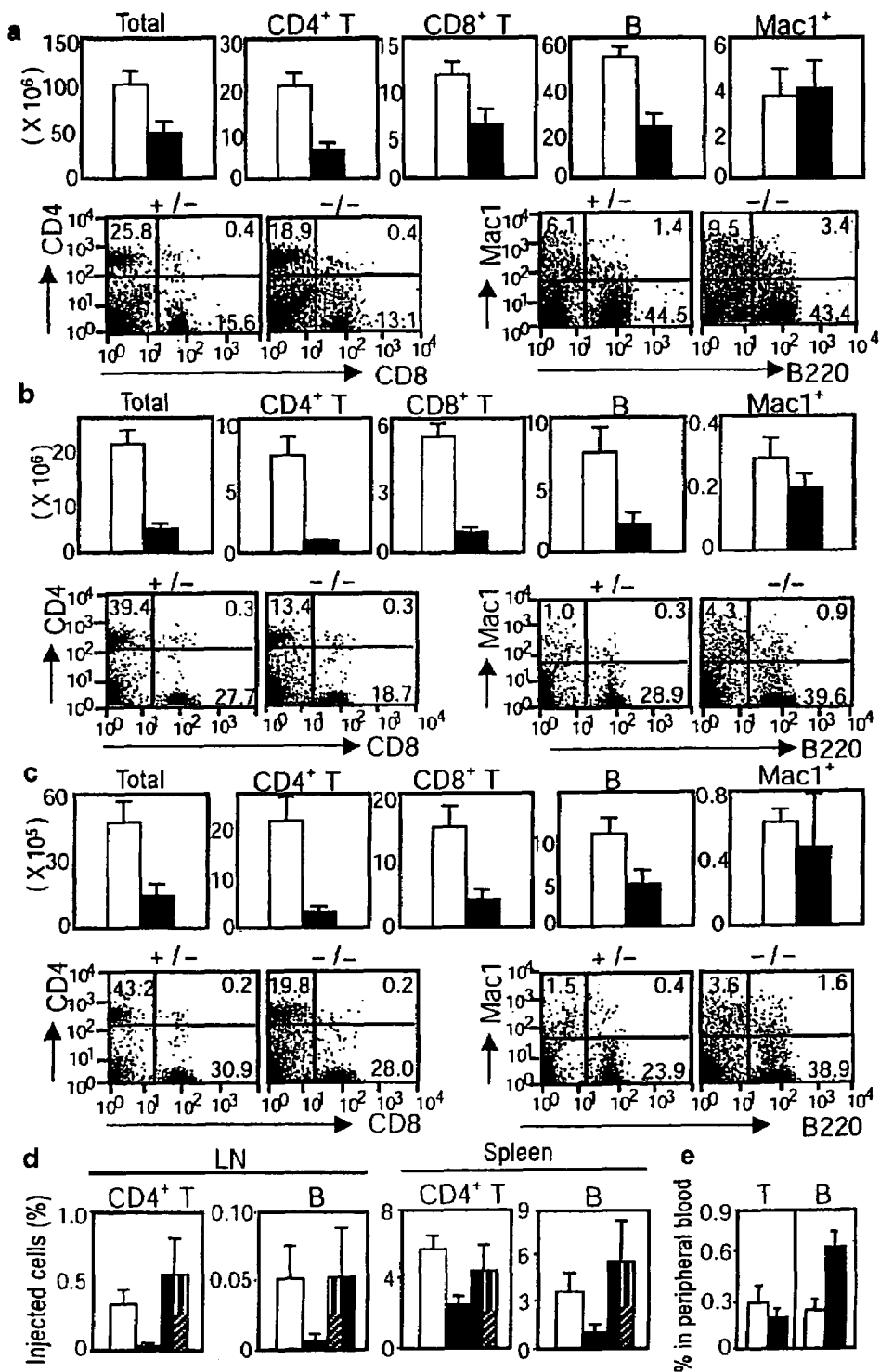

FIG. 2 is a series of graphs showing the results of examining the homing of DOCK2−/− mouse-derived lymphocytes to secondary lymphoid organs.

a-c: Spleen and lymph node cells were stained to detect CD4, CD8, B220 and Mac1. Figures (a), (b) and (c) show the number of total and each subset of cells in spleen, mesenteric lymph nodes and inguinal lymph nodes, respectively. Open bars in the figures denote cells from DOCK2$^{+/-}$ mice (n=4) and filled bars denote cells from DOCK2$^{-/-}$ mice (n=7 for a, n=4 for b and c).

d: Percentage of the fluorescence-labeled CD4$^+$ T and B cells in the inguinal lymph nodes and spleen at 48 h of the transfer was analyzed. Open bars in the figures denote the results of transferring cells from DOCK2$^{+/-}$ mice to C57BL/6 mice (n=4), filled bars represent the results of transferring cells from DOCK2$^{-/-}$ mice to C57BL/6 mice (n=5), and hatched bars represent the results of transferring cells from DOCK2$^{+/-}$ mice to DOCK2$^{-/-}$ mice (n=5).

e: Peripheral blood T or B cells were analyzed for the percentages (%) of the transferred cells 48 h after the transfer. Open bars in the figure represent the results of transferring cells from DOCK2$^{+/-}$ mice to C57BL/6 mice (n=7 for T cells, n=5 for B cells), and filled bars represent the results of transferring cells from DOCK2$^{-/-}$) mice to C57BL/6 mice (n=6).

Figure 3:
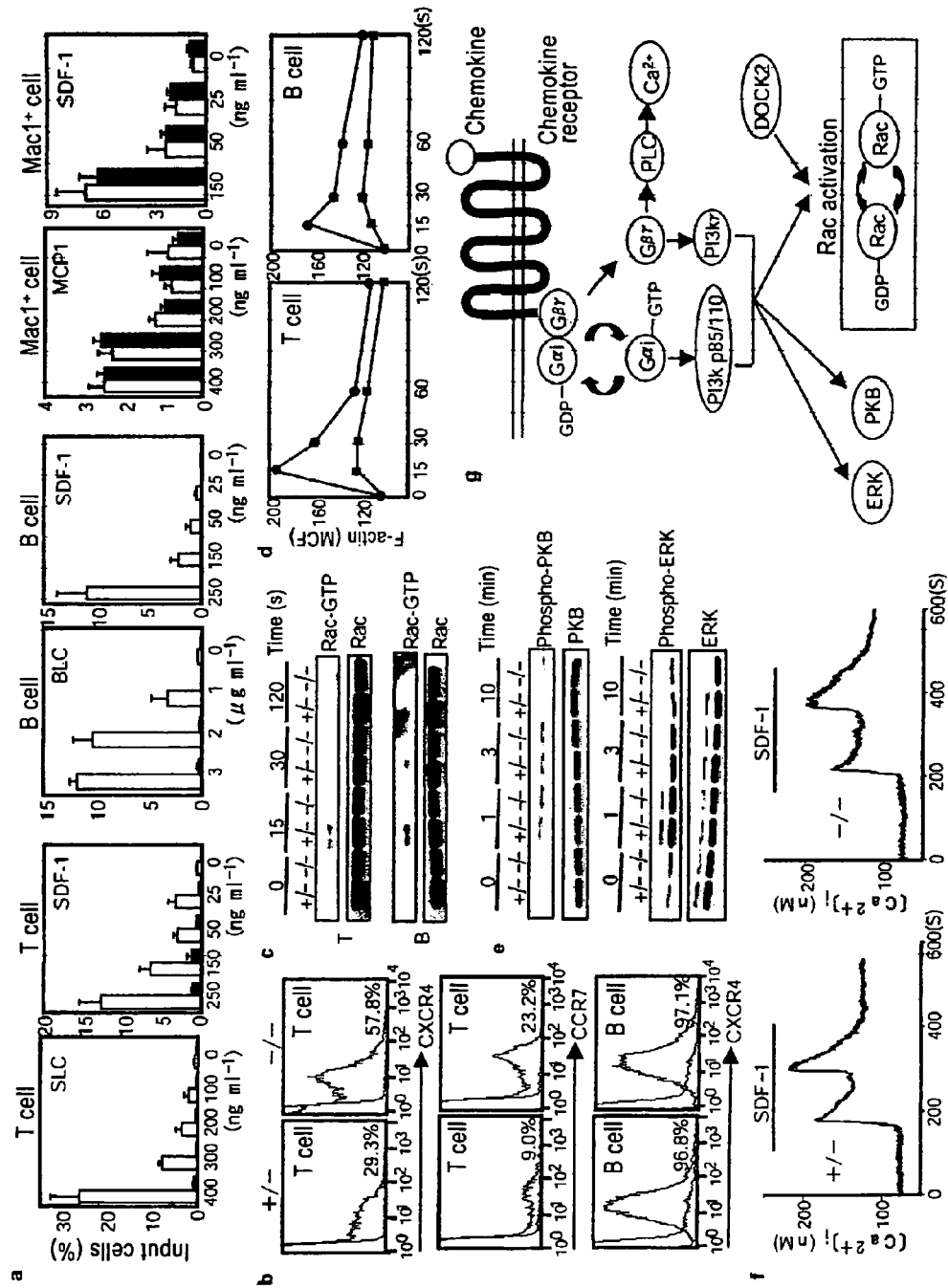

FIG. 3 is a photograph showing the analysis results of migration activity of the lymphocytes from DOCK2$^{-/-}$ mice of the present invention.

a: A transwell chemotaxis assay was carried out by using spleen cells from DOCK2$^{+/-}$ mice (open bars) and DOCK2$^{-/-}$ mice (filled bars). The results shown in the figures are expressed as the percentages to the input cells.

b: Spleen cells were stained with anti-CXCR4 or anti-CCR7 antibody (Blood 96, 2074-2080, 2000) ([1]; red lines), or with monoclonal antibodies against Thy1.2 or B220 ([2]; green lines) as control, to analyze receptor expression in Thy1.2$^+$ T cells or B220$^+$ B cells (graphs show relative cell numbers).

c: Splenic T and B cells (1.5×10$^7$) treated with SDF-1 (500 ng/ml) for the indicated times were analyzed for Rac activation using GST-fusion PAK1 RBD.

d: Splenic T and B cells (5×10$^6$) from DOCK2$^{-/-}$ (■) and DOCK2$^{+/-}$ (●) mice were treated with SDF-1 (500 ng/ml) for the indicated times and analyzed for the level of actin polymerization by flow cytometry. Results are expressed as the average of mean channel fluorescence (MCF) in three independent experiments, with the baseline fluorescence assigned a value of 100.

e: Splenic B cells (5-8×10$^6$) treated with SDF-1 (500 ng/ml) for the indicated times were analyzed for phosphorylation of PKB or ERK using the phospho-specific antibody against PKB (Ser$^{473}$) or ERK1 and ERK2 (Thr$^{202}$/Tyr$^{204}$), respectively.

f: Fura-2-loaded splenic B cells were treated with SDF-1 at 250 ng/ml, and [Ca$^{2+}$]$_i$ was measured with a digital fluorescence microscopy system.

g: Signaling pathways from chemokine receptor to Rac activation were schematized.

Figure 4:
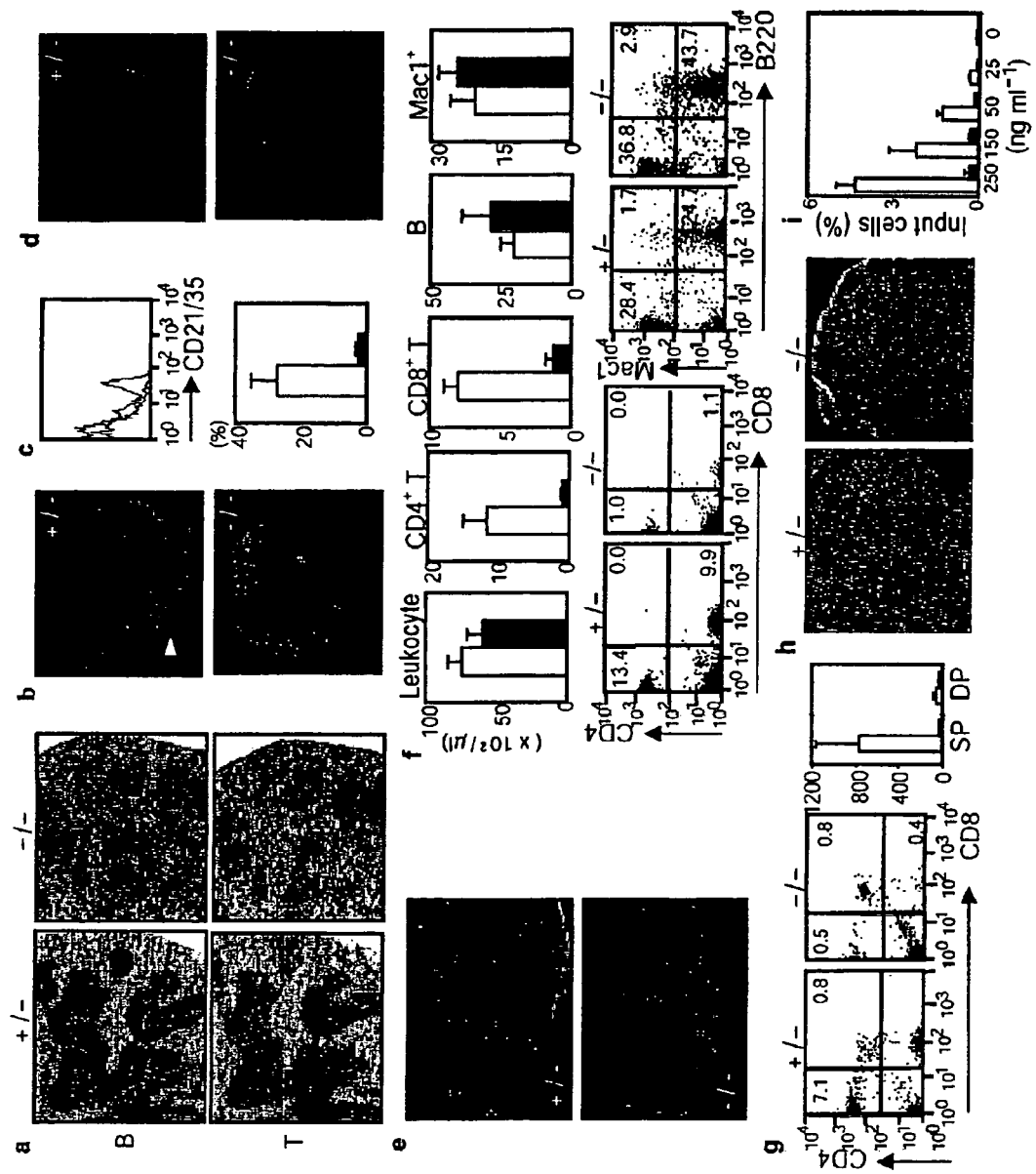

FIG. 4 is a series of photographs showing abnormal architecture of the immune system in DOCK2$^{-/-}$ mice of the present invention.

a: Sections for B cells (top panels) or T cells (bottom panels) were stained with anti-B220 antibody or anti-Thy1.2 monoclonal antibody, respectively.

b: Spleen sections were stained to detect B cells (green area), T cells (red area) and metallophilic macrophages (blue area) with anti-B220 antibody, a mixture of anti-CD4 and anti-CD8 monoclonal antibodies, and MOMA1. The arrowhead indicates marginal-zone B cells.

c: Spleen cells were stained to detect B220, CD23 and CD21/35, and B220$^+$CD23$^-$ B cells were analyzed for the CD21/35 expression (graph shows relative cell numbers). Flow cytometric profiles (top panel) in the gated spleen cell population of DOCK2$^{+/-}$ mice [[1] in the top panel (red line), and open bar in the bottom panel] and the spleen cell population of DOCK2$^{-/-}$ mice[[2] in the top panel (green line), and filled bar in the bottom panel], and the percentage of CD21/35$^+$ cells (bottom panel).

d: Lymph node sections were stained to detect B cells (green area) and T cells (red area) as in b.

e: Peyer's patches were stained to detect B cells (green area) and T cells (red area) as in b.

f: Blood samples were counted and stained to detect CD4, CD8, B220 and Mac1. The numbers of total and of each subset of peripheral blood leukocytes are determined. Open bars in the figures show the results for DOCK2$^{+/-}$ mice (n=4) and filled bars for DOCK2$^{-/-}$ mice (n=4).

g: Thymus organ cultures were used for transwell chemotaxis assays in the presence of ELC. Figures on the left show expression of CD4 and CD8 on the emigrated thymocytes and the figure on the right shows the numbers of CD4$^+$CD8$^-$ and CD4$^-$CD8$^+$ mature thymocytes (SP) and CD4$^+$CD8$^+$ thymocytes (DP) collected for 90 s from the thymus of DOCK2$^{+/-}$ (open bars, n=3) and DOCK2$^{-/-}$ mice (filled bars, n=3).

h: Thymus sections were stained to detect CD4 (green area) and CD8 (red area).

i: Chemotactic response of CD4$^+$CD8$^+$ thymocytes to SDF-1 was measured and compared between DOCK2$^{+/-}$ (open bars) and DOCK2$^{-/-}$ mice (filled bars) using a transwell chemotaxis assay. Results are expressed as percentages (%) of the input cells.

Figure 5:
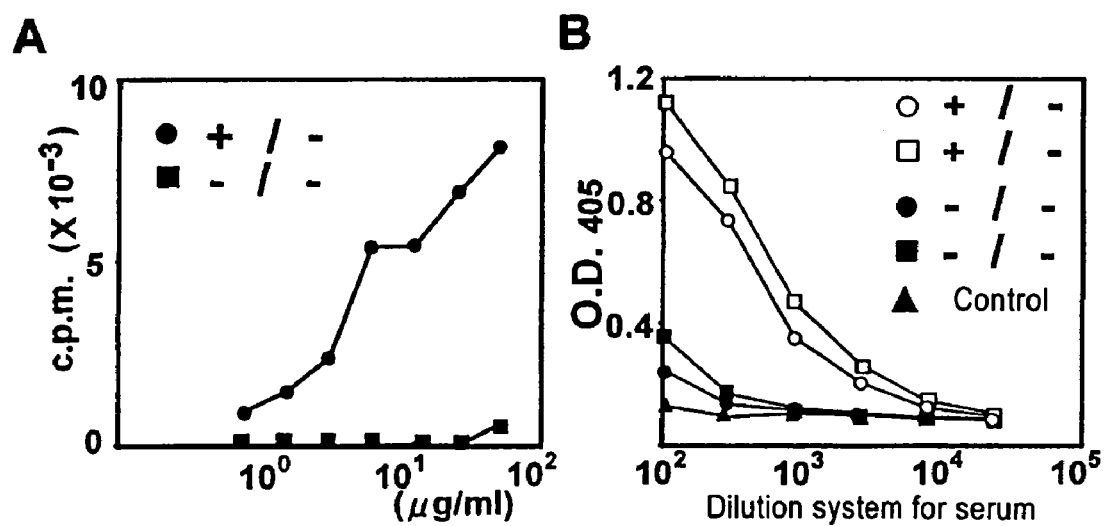

FIG. 5 shows suppression of immune-response in DOCK2$^{-/-}$ mice of the present invention.

a: Mice were immunized with an antigenic peptide derived from Eα together with an adjuvant and CD4$^+$ T cells were isolated from the regional lymph node 10 days after the immunization. The CD4$^+$ T cells were cultured in the presence of the peptide to analyze the T-cell proliferation. Vertical and horizontal bars show $^3$H-thymidine uptake and concentration of Eα-derived antigenic peptide.

b: DNP-KLH was immunized with an adjuvant and the blood was collected on day 7 of the immunization. Antigen-specific IgG in the serum was qualified using an enzyme-antibody method. Vertical and horizontal bars show OD450 levels and dilution system for the serum, respectively.

BEST MODE OF CARRYING OUT THE INVENTION

Any animal model whose function to control lymphocyte migration is lacked or suppressed by deleting its DOCK2 gene on the chromosome may be used as a nonhuman animal model lacking the function to control lymphocyte migration. The function of DOCK2 gene can be deleted on its chromosome, for example, by inactivating the function by a gene mutation procedure in which whole or part of a nonhuman animal endogenous gene encoding DOCK2 is disrupted, deleted or substituted and the like. Nonhuman animals for the present invention may include rodents such as mice, rats,etc. and also include rabbits, dogs, pigs, sheep, monkeys, etc. The nonhuman animals, of course, will not be limited to these examples, and mice are preferred among these examples because they are easily handled and so on. As for the DOCK2 gene mentioned above, Hch (mouse DOCK2) gene (GenBank accession No. AYO27438; Nature, Vol412, 23 August, 826-831, 2001) and human DOCK2 gene (KIAA0209; DNA Res. 3, 321-329) can be exemplified, yet the origin of DOCK2 gene is not limited to mice, human and so on.

The function to control lymphocyte migration in the nonhuman animal model lacking the function to control lymphocyte migration according to the present invention will not be limited to any particular function as long as it is a function to control lymphocyte mobility affected by gene expression of DOCK2. Yet the following functions are the examples; a function to promote reorganization of cytoskeleton, particularly actin polymerization in lymphocytes, through Rac activation for the formation of Rac-GTP complex, migration function of lymphocytes through stimuli with chemokines such as SLC, SDF-1, BLC, etc., homing function to secondary lymphoid organs such as spleen, lymph nodes and Peyer's patches, emigration function of mature thymic T cells into peripheral blood in response to chemokine stimulus with ELC, migration function of $CD4^+$ $CD8^+$ immature thymocytes in response to chemokine stimulus with SDF-1, and so on. In the nonhuman animal models lacking the function to control lymphocyte migration of the present invention in which the functions to control lymphocyte migration is deleted or suppressed, actin polymerization in lymphocytes in response to chemokine stimuli is almost totally abolished, and these nonhuman animal models of the present invention are animal models, preferably DOCK2 knockout mice, in which marked atrophy of lymphoid follicles, straying of lymphocytes into red pulp, and disappearance of marginal-zone B cells are observed. The following is the description taking mice as an animal model.

A method for generating mice in which DOCK2 gene is deficient on its chromosome, i.e. DOCK2 knockout mice ($DOCK2^{-/-}$ mice), will not be limited to a particular method and the mice can be generated by, for example, a method previously described (Cell 76, 519-529, 1994) and the like. For instance, DOCK2 gene is screened using gene fragments obtained by PCR method or the like from the mouse genomic library. Whole or part of the screened DOCK2 gene is substituted by, e.g., a marker gene such as neomycin-resistant gene using a recombinant DNA technology, then a gene such as a diphtheria toxin A fragment (DT-A) gene or a herpes simplex virus thymidine kinase (HSV-tk) is introduced into the 5' terminal to obtain a targeting vector. The targeting vector thus obtained was linearized and introduced into ES cells by electroporation or the like to cause homologous recombination. ES cells resistant to antibiotics such as G418, gancyclovir (GANC) are selected from among the homologous recombinants. The selected ES cells are preferably subjected to southern blotting or the like to confirm whether they are the recombinants of the target.

The recombinant ES cells above are microinjected into mouse blastocysts and the blastocysts are transplanted to recipient mice to generate chimeric mice. Intercrossing of the chimeric and wild-type mice gives heterozygous mice, and further intercrossing of these heterozygous mice gives DOCK2 knockout mice. Whether DOCK2 gene is actually deficient on the chromosome in such DOCK2 knockout mice can be confirmed by methods like southern blotting wherein isolated DNA from tails of the mice thus obtained is analyzed, immunoblotting wherein proteins extracted from lymphocytes or the like of the mice are analyzed, and so on.

Nonhuman animal models lacking the function to control lymphocyte migration of the present invention are highly useful as animal models for elucidating immune-related diseases and pathogenic conditions such as allergy, autoimmune diseases, GvH and graft rejections, or as animal models for developing a new therapy for these diseases and pathogenic conditions. Comparison between mice lacking the function to control lymphocyte migration and wild-type mice with the use of the nonhuman animal models lacking the function to control lymphocyte migration enables to screen promoters or suppressors of the function to control lymphocyte migration with DOCK2 as a target and to screen a therapeutic agent for immune-related diseases such as allergy, autoimmune diseases, GvH and graft rejections.

Method for screening promoters or suppressors of the function to control lymphocyte migration of the present invention include a method wherein a test substance is administered to the aforementioned nonhuman animal model lacking the function to control lymphocyte migration of the present invention, and a method wherein a test substance and tissues, organs or cells of a nonhuman animal model lacking the function to control lymphocyte migration are brought into contact. As a method to bring a test substance and tissues, organs or cells of a nonhuman animal model lacking the function to control lymphocyte migration, e.g. the DOCK2 knockout mouse aforementioned, and a wild-type animal into contact, there is a method to bring a test substance and tissues, organs or cells of these animals into contact, and to determine/assess change in the function to control lymphocyte migration such as changes in active Rac bound to GTP, in cellular polarity such as uneven nuclear distribution, in actin polymerization, in migration activity of lymphocytes in response to stimuli with chemokines such as SLC, SDF-1 and BLC. Examples of methods for administrating a test substance to a nonhuman animal model lacking the function to control lymphocyte migration, e.g. the aforementioned DOCK2 knockout mouse, and to a wild-type animal include a method for measuring/assessing changes in the function controlling lymphocyte migration in the tissue, organ or cells of the mice, for example, change in active GTP-bound Rac in cells such as lymphocytes, change in cellular polarization such as uneven nuclear distribution, change in actin polymerization, change in migration activity of lymphocytes in response to stimuli with chemokines such as SLC, SDF-1 and BLC in the mice, change in homing activity into secondary lymphoid organs such as spleen, lymph nodes and Peyer's patches, change in the number of mature T cells in peripheral blood in response to stimulus with chemokine ELC, change in migration activity of $CD4^+$ $CD8^+$ immature tymocytes in peripheral blood in response to stimulus with chemokine SDF-1, or the degrees of change in atrophy of lymphoid follicles, straying of lymphocytes into red pulp, and disappearance of marginal-zone B cells. The methods, however, will not be limited only to these examples.

In performing screening described above, promoters or suppressors of the function to control lymphocyte migration, especially suppressors, can be efficiently screened by using molecules binding to DOCK2 in vitro or the like, preferably molecules specifically binding to DOCK2, as a test substance. Methods for searching molecules binding to DOCK2 in vitro or the like preferably include those conventionally known search methods for interacting proteins such as two-hybrid system using yeast, far western method using *E. Coli* expression system, immunoprecipitation method, and a method using affinity chromatography. Further, in performing the above-described screenings, it is preferable to compare/assess the degree of change in the function to control lymphocyte migration of nonhuman animals lacking DOCK2 gene on the chromosome and the degree of change in that of wild-type nonhuman animals, preferably in that of their littermate nonhuman animals.

With the use of the above-described methods for screening promoters or suppressors of the function to control lymphocyte migration, screening for therapeutic agents for treating immune-related diseases such as allergy, autoimmune diseases, GvH and graft rejections can be made possible. For instance, suppressors of the function to control lymphocyte migration including anti-DOCK2 antibody, DOCK2-binding molecule, an antisense strand of DOCK2 gene obtained by the method for screening promoters or suppressors of the function to control lymphocyte migration are expected to artificially suppress lymphocyte trafficking, so that these suppressors are highly promising for therapeutic agents for treating immune-related diseases such as allergy, autoimmune diseases, GvH and graft rejections. When therapeutic agents are used as medical products, various compounding components for formulation can be added such as common carriers, binders, stabilizers, excipients, dilutions, pH-buffers, disintegrants, solubilizers, solubilizing adjuvants, isotonic agents, that are pharmaceutically acceptable. The therapeutic agents can be administered in an usually used formulation, for example by oral administration in forms of powders, granules, capsules, syrups, suspensions or the like, or by parenteral administeration in the form of injections formulated to solutions, emulsions, suspensions, etc.

The present invention targets proteins controlling lymphocyte migration that promote reorganization of cytoskeleton through activating Rac, or DNAs encoding such proteins controlling lymphocyte migration. The present invention also targets the use of the proteins controlling lymphocyte migration that promote reorganization of cytoskeleton through activating Rac for the purpose of controlling lymphocyte migration, and a method using DNAs encoding the proteins controlling lymphocyte migration for the purpose of expressing the proteins controlling lymphocyte migration. Specific examples of such proteins or DNAs are DOCK2 such as Hch, or DOCK2 gene such as Hch gene (GenBank: accession No. AYO27438). As described in the above, the function of the proteins controlling lymphocyte migration that promote reorganization of cytoskeleton through Rac activation, or the function of DNAs encoding such proteins controlling lymphocyte migration have never been revealed before having elucidated by the present invention.

The present invention will be explained more specifically with reference to the following examples, the technical scope of the invention, however, will not be limited to these exemplifications.

EXAMPLE 1

Reorganization of Actin Cytoskeleton Mediated by DOCK2 in the T-cell Line

DOCK2 gene (KIAA0209; DNA Res. 3, 321-329) is known to encode CDM family proteins specifically expressed in human haematopoietic cells. Although DOCK2 has been shown to bind to and activate Rac in 293T kidney cells (Biochem. Biophys. Acta 1452, 179-187, 1999), its physiological function remained unknown.

In an attempt to search the genes that are expressed in the mouse thymus, the present inventors isolated complementary DNA, designated as Hch gene (GenBank accession number: AYO27438), which predictably encodes 1828 amino acids including SH (Src-homology)-3 domain at the amino terminus and found that Hch was homologous to CED-5, MBC and DOCK180; furthermore, 1677 of the 1828 amino acids of Hch were identical to human DOCK2. Whereas DOCK180 was expressed in various tissues, the expression of Hch was restricted to thymus, spleen and lymph nodes, suggesting that Hch is specifically expressed in haematopoietic cells. The Hch expression was detected in all T-, B- and monocyte cell lines tested, with the exception of two T-cell lines, BW5147$\alpha^-\beta^-$ and its derivative BE$\alpha$16-3 (referred to as "16-3" hereinafter). From these results, the present inventors concluded that Hch gene is a mouse homologue of human DOCK2 gene.

Figure 1:
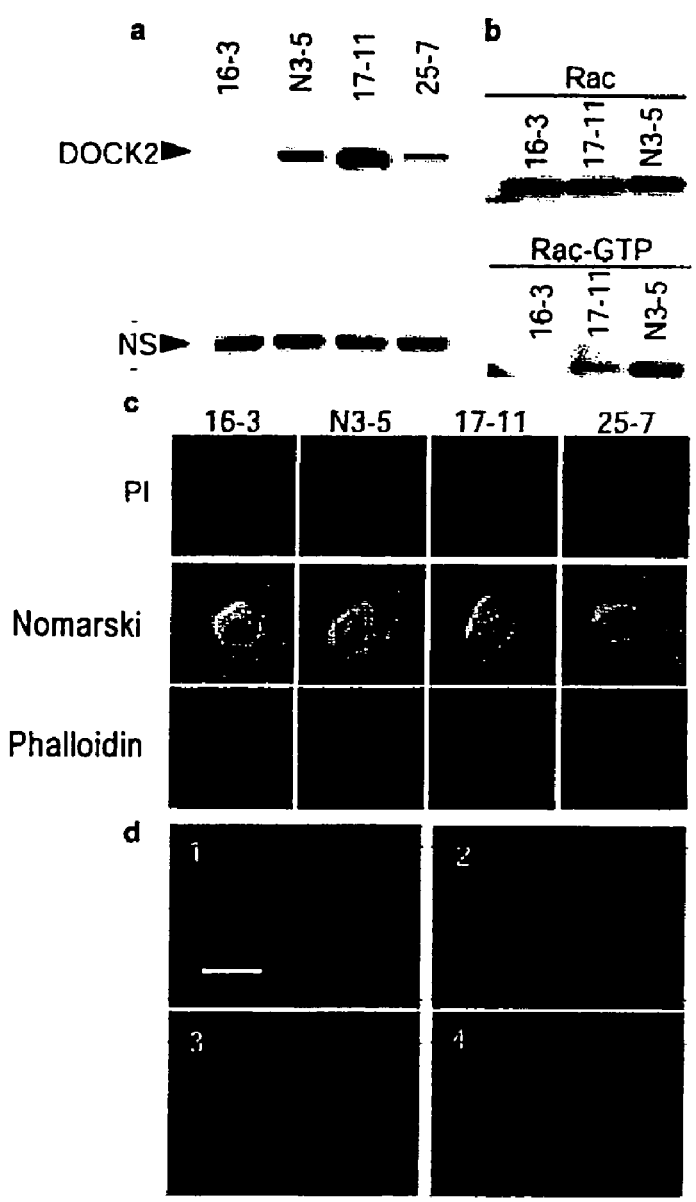
FIG. 1 is a series of photographs showing the results of reorganization of actin cytoskeleton caused by DOCK2 in a T-cell line.

Whether the expression of DOCK2 gene affects the actin cytoskeleton was first examined by introducing mouse DOCK2 gene into the T-cell line 16-3 which lacks DOCK2 gene. As a result of western blot analysis, two cell lines stably expressing transgenes, 17-11 and 25-7, showed slightly higher (17-11) or lower (25-7) expression compared with a wild-type cell line N3-5 (FIG. 1$a$). The active GTP-bound Rac, which interacts with PAK1 (Nature 367, 40-46, 1994), was detected with 17-11 and N3-5, but not with 16-3 (FIG. 1$b$). In several aspects, the present inventors found that cell lines 17-11 and 25-7 were morphologically different from 16-3, but were similar to N3-5. Although 16-3 had a round cell shape, 17-11, 25-7 and N3-5 showed a relatively flat and polarized cell shape with a biased localization of the nucleus (FIG. 1$c$). When cells were stained with phalloidin, F-actin assembly was observed in 17-11, 25-7 and N3-5, but not in 16-3 (FIG. 1$c$). The confocal laser microscopic analysis revealed that the introduced DOCK2 did not co-localize with, but was located adjacent to, this F-actin assembly at the root of the lamellipodial protrusion (FIG. 1$d$). Thus it was revealed that, like other CDM family proteins, DOCK2 mediates reorganization of actin cytoskeleton in T cells through Rac activation.

EXAMPLE 2

Generation of DOCK2$^{-/-}$ Mice

Genomic clones containing the mouse DOCK2 gene were isolated from a 129/Sv genomic library. The targeting vector was constructed by replacing a 3.1 kb fragment from the KpnI site located within exon 3 to the BamHI site between exon 5 and 6 with a neomycin resistance cassette (neo). This vector was linearized and subjected to electroporation, then introduced into ES cells to generate homologous recombinants. ES clones were isolated from these homologous recombinants, the neomycin-resistance ES clones were then screened by using G418. The homologous recombinants were confirmed by southern blotting. Genomic DNAs were isolated from these homologous recombinants and were digested with Sph I and Eco RI, then the DNAs were confirmed to have been replaced by targeting alleles containing neo cassettes. After the confirmation, the targeted ES clones were microinjected into C57BL/6 blastocysts and the male chimeric mice obtained were crossed with C57BL/6 female mice. The heterozygous mice (DOCK2$^{+/-}$) with mutant alleles were intercrossed to obtain DOCK2$^{-/-}$ mice. Southern blot analysis confirmed that wild-type DOCK2 alleles were specifically disrupted in mutant mice (DOCK2$^{+/-}$ mice). RT-PCR (polymerase chain reaction with reverse transcription) revealed that insertion of the neo cassette results in the appearance of a stop codon at the N-terminus portion of DOCK2, leaving only 42 amino-acid residues. DOCK2 expression was not detected in the spleen and thymus of mutant mice in a western blot analysis. In the following experiments, the DOCK2$^{+/-}$ and DOCK2$^{-/-}$ littermate mice were used.

EXAMPLE 3

Defect in Homing of DOCK2$^{-/-}$ Mouse-derived Lymphocytes to Secondary Lymphoid Organs To investigate the physiological function of DOCK2, the present inventors generated DOCK2-deficient mice by homologous recombination in embryonic stem (ES) cells. DOCK2$^{-/-}$ mice were born at the expected mendelian ratio without apparent abnormality. However, the total number of spleen cells in DOCK2$^{-/-}$ mice was reduced to about 50% of that in DOCK2$^{+/-}$ mice (FIG. 2a). Although the proportion of CD4$^+$ and CD8$^+$ T cells, and also B cells, were not much changed in DOCK2$^{-/-}$ mice from that of DOCK2$^{+/-}$ mice in the spleen cells, the proportion of Mac1$^+$ monocytes was significantly increased in DOCK2$^{-/-}$ mice. A similar tendency was observed with mesenteric and inguinal lymph node cells, except for the proportion of CD4$^+$ T cells (FIGS. 2b, c): Whereas CD4$^+$ T cells occupied approximately 40% of lymph node cells in DOCK2$^{+/-}$ mice, this proportion decreased to less than 25% in DOCK2$^{-/-}$ mice. Collectively, the total numbers of T- and B-cells, but not monocytes, were markedly reduced in the spleen and lymph nodes of DOCK2$^{-/-}$ mice.

These findings raised the possibility that lymphocyte homing to secondary lymphoid organs might be impaired in DOCK2$^{-/-}$ mice. To address this issue, the present inventors compared and investigated chemotaxis of fluorescence-labeled CD4$^+$ T- or B-cells to the peripheral lymph nodes or spleen. When cells prepared from DOCK2$^{+/-}$ mice were injected intravenously into wild-type mice (C57BL/6), 0.34 and 0.05% of the injected CD4$^+$ T- or B-cells, on average, migrated to the inguinal lymph nodes, respectively (FIG. 2d, left). However, when cells prepared from DOCK2$^{-/-}$ mice were injected to wild-type mice, the percentages of the migrated CD4$^+$ T- or B-cells were reduced to about 10% of the level observed upon injecting cells from DOCK2$^{+/-}$ mice. A similar difference was found on analysis of migration to the wild-type spleen (FIG. 2d, right). On the other hand, CD4$^+$ T- and B-cells prepared from DOCK2$^{+/-}$ mice efficiently migrated to the inguinal lymph nodes and spleen of DOCK2$^{-/-}$ mice (FIG. 2d). These results suggested that lymphocyte homing is impaired in DOCK2$^{-/-}$ mice owing to an intrinsic defect in lymphocytes. Although no significant differences were found in the expression frequency of transferred T cells in the peripheral blood of wild-type mice, the percentage of the transferred mouse DOCK2$^{-/-}$ B cells showed a 2.7-fold increase in level compared with the mouse DOCK2$^{+/-}$ B cells (FIG. 2e).

EXAMPLE 4

Defect in Migration Activity in DOCK2$^{-/-}$ Mice-derived Lymphocytes

What was analyzed next was chemotaxis of splenic T- and B cells in response to stimuli with several chemokines, such as secondary lymphoid organ chemokine (SLC), B-lymphocyte chemoattractant (BLC), stroma-derived factor (SDF)-1 and monocyte chemotactic protein (MCP)-1. Whereas T- and B-cells from DOCK2$^{+/-}$ mice efficiently migrated in response to SLC, SDF-1 and BLC, those from DOCK2$^{-/-}$ mice did not show any response to stimuli with these chemokines (FIG. 3a, left and middle). In contrast, chemotactic response was observed in the DOCK2$^{-/-}$ mouse monocytes in response to stimuli with MCP-1 and SDF-1, and a similar chemotactic response was also observed in monocytes from DOCK2$^{+/-}$ mice (FIG. 3a, right). Since some reports demonstrate that the chemotactic activities of SLC and SDF-1 are induced through interaction with their receptors, CCR7 or CXCR4, respectively (Nature 382, 829-833, 1996; Nature 382, 833-835, 1996; J. Biol. Chem. 273, 7118-7122, 1998), the expressions of CXCR4 or CCR7 on the surface of splenic B cells and on splenic T cells were analyzed. The result showed that splenic B cells from DOCK2$^{-/-}$ and DOCK2$^{+/-}$ mice comparably expressed CXCR4 on their surface, and that the expressions of CXCR4 and CCR7 on splenic T cells were even higher in DOCK2$^{-/-}$ than in DOCK2$^{+/-}$ mice (FIG. 3b). Thus it is clear that the defect in chemotactic response of DOCK2$^{-/-}$ lymphocytes does not result from extremely low, or absence of, receptor expression. Taken together, these results indicate that although DOCK2 is not involved in monocyte migration, DOCK2 molecules are indispensable for lymphocyte migration by functioning in the downstream of chemokine receptors.

Chemokine receptors are coupled with heterodimeric $G_i$ proteins that activate a variety of signaling pathways. Phosphatidylinositol-3-OH kinases (PI(3)K) in the downstream of the chemokine receptors are essential signaling molecules involved in activation of Rac, protein kinase B (PKB) and extracellular signal-regulated kinases (ERKs) (Immunol. Rev. 177, 217-235, 2000, Nature Immunol. 2, 129-134, 2001). When T cells and B cells from DOCK2$^{+/-}$ mice were stimulated with SDF-1, the activated Rac was detected. Such activation, however, was totally abolished in DOCK2$^{-/-}$ lymphocytes (FIG. 3c). Consistent with this result, SDF-1-induced actin polymerization was observed in DOCK2$^{+/-}$ lymphocytes, but was scarcely detected in DOCK2$^{-/-}$ lymphocytes (FIG. 3d). In contrast, SDF-1-induced phosphorylations of PKB, ERK1 and ERK2 were comparable between both DOCK2$^{+/-}$ and DOCK2$^{-/-}$ B cells (FIG. 3e). It is known that Chemokines can also activate phospholipase C leading to an increase in intracellular Ca$^{2+}$ concentration [Ca$^{2+}$] (Nature Immunol. 2, 129-134, 2001). As a result of examining inflow of Ca$^{2+}$ induced by SDF-1, such inflow was revealed to occur to a similar extent in both DOCK2$^{+/-}$ and DOCK2$^{-/-}$ B cells (FIG. 3f). These results indicate that in chemokine receptor-mediated signaling pathways DOCK2 is predominantly involved in Rac activation (FIG. 3g).

EXAMPLE 5

Abnormal Architecture of the Immune System in DOCK2$^{-/-}$ Mice

The immuno-chemokines such as SLC and BLC are known to be critical for trafficking of lymphocytes into subcompartments of secondary lymphoid organs (Cell 87, 1037-1047, 1996, Blood 91, 2886-2895, 1998, Cell 99, 23-33, 1999, J. Exp. Med. 189, 451-460, 1999). As lymphocytes from DOCK2$^{-/-}$ mice lacked chemotactic response to these chemokines in vitro, spleen, lymph nodes and Peyer's patches were also examined. In the spleen of DOCK2$^{+/-}$ mice, lymphoid follicles that consisted of T-cell zone and the surrounding B-cell area were clearly defined (FIG. 4a, left). However, such lymphoid follicles were quite atrophic in the DOCK2$^{+/-}$ mouse spleens, and scattered distribution of lymphocytes (T and B cells) in red pulp was observed in this line (FIG. 4a, right). Immunofluorescence analysis of splenic tissue sections revealed that marginal-zone B cells, normally distributed around metallophilic macrophages, were markedly reduced in DOCK2$^{-/-}$ mice (FIG. 4b). The marginal-zone B cells can be characterized as CD21/CD35$^{high}$CD23$^{neg-low}$ B cells (Eur. J. Immunol. 27, 2366-2374, 1997). Although around 25-30% of B220$^{+}$ CD23$^{-}$ splenic B cells expressed CD21/CD35 in DOCK2$^{+/-}$ mice, such population of B cells was scarcely found in DOCK2$^{-/-}$ mice, confirming the defect of marginal-zone B cells in DOCK2$^{-/-}$ line (FIG. 4c). The atrophy of lymphoid follicles and aberrant T-cell distribution were also observed in lymph nodes of DOCK2$^{-/-}$ mice (FIG. 4d). In addition, it was also found that Peyer's patches were poorly developed in DOCK2$^{-/-}$ mice in terms of seize and cell density (FIG. 4e).

SDF-1 serves as a chemoattractant for immature lymphocytes. The chemotactic responses of DOCK2$^{-/-}$ pro-B and pre-B cells to SDF-1 (250 ng/ml) were significantly reduced compared with those of DOCK2$^{+/-}$ mice (3.4% versus 18.5% in pro-B cells; 0.5% versus 5.6% in pre-B cells, respectively). However, the amounts of pro-B cells, pre-B cells, immature B cells and myeloid cells in the bone marrow were unchanged between in DOCK2$^{+/-}$ and DOCK2$^{-/-}$ mice. This indicates that DOCK2 deficiency affects neither B lymphopoiesis nor myelopoiesis. Although the total number of thymocytes and the proportion of CD4$^{-}$CD8$^{-}$ thymocytes in DOCK2$^{-/-}$ mice decreased and increased, respectively, compared with those in DOCK2$^{+/-}$ mice, the proportion of mature thymocytes in these lines were comparable. Nontheless, the total number of CD4$^{+}$ and CD8$^{+}$ T cells in peripheal blood decreased extremely in DOCK2$^{-/-}$ mice (FIG. 4f). Thymocyte migrations in DOCK2$^{+/-}$ and DOCK2$^{-/-}$ mice in response to EBI1-ligand chemokine (ELC), which is known to function as a chemoat-tractant for mature thymocytes, were compared (Blood 91, 4434-4443, 1998). Although CD4$^{+}$CD8$^{-}$ and CD4$^{-}$ CD8$^{+}$ mature thymocytes from the DOCK2$^{+/-}$ thymus efficiently emigrated, mature thymocytes were scarcely detected in the case of DOCK2$^{-/-}$ mice (FIG. 4g, left). The efficacy of mature thymocyte emigration from the thymus of DOCK2$^{-/-}$ mice was reduced to less than 5% of the wild-type level (FIG. 4g, right). It is thus suggested that an emigration defect of mature thymocytes to the peripheral bloodstream is responsible for T lymphocytopenia observed in DOCK2$^{-/-}$ mice. It was confirmed that in the thymus of DOCK2$^{-/-}$ mice, CD4$^{+}$CD8$^{-}$ and CD4$^{-}$CD8$^{+}$ mature thymocytes were distributed irregularly throughout the thymus as small patches (FIG. 4h). Although the precise mechanism for this currently remains unknown, thymocyte trafficking within the thymus may also be impaired in DOCK2$^{-/-}$ mice. This could also be evidenced by the fact that the chemotactic response of CD4$^{+}$CD8$^{+}$ immature thymocytes to SDF-1 was severely impaired in DOCK2$^{-/-}$ mice (FIG. 4i).

EXAMPLE 6

Defect in Immune-response of DOCK2$^{-/-}$ Mice

To assess the influence of DOCK2 defect on immune-response, DOCK2$^{-/-}$ and DOCK2$^{+/-}$ mice were immunized at their tail undersides with 50 g of Eα-derived peptide, which is known to bind to MHC class II I-A$^{b}$, together with an adjuvant. Ten days after the immunization, CD4$^{+}$ T cells were isolated from the regional lymph node and cultured in the presence of Eα-derived peptide in vitro to analyze the antigen-specific T cell response. T cells were observed to proliferate in a peptide concentration-dependent manner in wild-type mice, whereas in DOCK2$^{-/-}$ mice no such response of T cells was observed. Further, DNP-KLH was similarly immunized to analyze production of KLH-specific antibodies, as a result, the antibody production in DOCK2$^{-/-}$ mice was significantly impaired on day 7 after the immunization. That is to say, it was revealed that primary immune-response was impaired in DOCK2$^{-/-}$ mice.

These observation results demonstrate that haematopoi-etic cell-specific CDM family protein DOCK2 functions as a main molecule that activates Rac and mediates cytoskeletal reorganization in lymphocyte migration. Several abnormalities that were observed in DOCK2$^{-/-}$ mice were similar to those of mice that lacked CCR7, SLC or CXCR5 (the receptor cells for BLC) (Cell 87, 1037-1047, 1996, Blood 91, 2886-2895, 1998, Cell 99, 23-33, 1999, J. Exp. Med. 189, 451-460, 1999). However, DOCK2$^{-/-}$ mice exhibited abnormalities in a broader range in that they showed phenotypes that are not observed in the above-mentioned deficient mice such as T lymphocytopenia, loss of marginal-zone B cells, abnormal thymus architecture and reduced lymphocyte homing to the spleen. Some of these features probably reflect unresponsiveness of lymphocytes from DOCK2$^{-/-}$mice to other unknown chemokines or chemokines having undefined function. Furthermore, because of its nature to regulate the actin cytoskeleton, DOCK2 may not merely be involved in chemokine-mediated lymphocyte migration but also in other higher functions of lymphocytes.

Method 1 (Preparation of Cells That Stably Express Transgenes)

A full-length DOCK2 gene, or a full-length DOCK2 gene fused with an influenza hemagglutinin (HA) peptide tag was inserted into a PBJ1-expressing vector and transferred to 16-3T cell lines by electroporation.

Method 2 (Immunoblot Analysis)

Anti-mouse DOCK2 polyclonal antibody was developed by immunizing rabbits with carboxy-terminal peptide of DOCK2 to which a keyhole limpet haemocyanin is conjugated, and this was used to detect DOCK2 expression. To assess Rac activation, cell extracts were incubated in the presence of the glutathione S-transferase (GST)-fusion and Rac-binding domain (RBD) of PAK1, and subjected to immunoblot analysis using anti-Rac monoclonal antibody (Upstate Biotechnology). Activity of PKB or ERK was assessed with phospho-specific antibodies against PKB (Ser$^{473}$) or ERK1 and ERK2 (Thr$^{202}$/Tyr$^{204}$), respectively (Cell Signalling).

Method 3 (Immunofluorescent Microscopy)

Cells were fixed with 4% formaldehyde in phosphate-buffered saline (PBS), permeabilized with 0.1% saponin and stained with propidium iodide (CALBIOCHEM), Alexa 568-labeled phalloidin (Molecular Probes) and/or anti-HA antibody (Santa Cruz) followed by Alexa 488-labeled anti-rabbit immunoglobulin (Ig)-γ. The staining profiles were visualized with either a fluorescence microscope equipped with Nomarski optics or a confocal laser-scanning microscope equipped with an argon/krypton laser capable of dual excitation.

Method 4 (Blood Counts and Flow Cytometric Analysis)

Blood was obtained by retro-orbital venous plexus puncture and subjected to an analysis on an automatic cell counter. Cell counts were determined for bone marrow cells, thymocytes, spleen cells and lymph node cells using Neubauer chambers. Flow cytometry was carried out by staining the cells with the relevant monoclonal antibodies (PharMingen) and analyzing them on a FACScan (Becton-Dickinson). To assess actin polymerization, purified T and B cells were fixed with 4% paraformaldehyde in PBS, treated with 0.1% saponin, and stained with Alexa 488-labeled phalloidin for flow cytometry.

Method 5 (Tissue Staining)

Cryostat sections were fixed in acetone and 1% paraformaldehyde, and stained with Alexa 488- or 594-labeled monoclonal antibodies. Staining with anti-metallophilic macrophage monoclonal antibody (MOMA1) was followed by reaction with biotinylated anti-rat IgG antibody and reacted and stained with streptavidin-conjugated Cy5.5. In some experiments, tissue sections were stained with biotinylated monoclonal antibodies and visualized with a Vectastain ABC-PO kit (Vector Laboratories).

Method 6 (Lymphocyte Homing Assay)

Purified $CD4^+$ T or B cells ($4 \times 10^7$ ml) were labeled with 3 μM BCECF-AM solution (Dojindo), washed with PBS and intravenously injected into mice ($8 \times 10^6$ to $1 \times 10^7$ per mouse). After 48 h, cells were prepared from the spleen and inguinal lymph nodes, and counted. Before and after the cell transfer, cells were stained with anti-CD4 or anti-B220 monoclonal antibody, and the percentage of migrated cells (%) was calculated. The percentages of transferred T and B cells in peripheral blood were calculated by staining the cells with anti-Thy1.2 or anti-B220 monoclonal antibody 48 after the transfer.

Method 7 (Chemotaxis Assay)

Thymus organ, spleen cells ($1.5 \times 10^6$), bone marrow cells ($1.5 \times 10^6$) and thymocytes ($1.5 \times 10^6$) in 100 μl RPMI medium were loaded into transwells (Coaster, 5-μm pore size), which were placed onto 24-well plates containing 450 μl RPMI medium supplemented with chemokines (Genzyme/Techne) at various concentrations. After 3 h of incubation at 37° C., cells migrated to the lower chamber were collected and stained with the relevant antibodies. Cells were counted with a FACScan.

Method 8 (Measurement of Intracellular $Ca^{2+}$ Concentration)

$[Ca^{2+}]_i$ was measured using the Attofluor (fluorescent dye) digital fluorescence microscopy system (Carl Zeiss). Cells loaded with fura-2/AM (Dojindo) were put in a chamber of 0.5-ml volume and mounted on an inverted microscope. The measurement of intracellular $Ca^{2+}$ concentration was performed while the bath was continuously perfused with a modified Krebs solution (pH 7.3). The fura-2 fluorescence images were recorded into a re-writable optical disc recorder at a rate of roughly 1 Hz and converted to $Ca^{2+}$ concentration.

Method 9 (Analysis of Immune-response)

Mice were immunized with an antigenic peptide together with an adjuvant at the underside of tails, and $CD4^+$ T cells were isolated from the regional lymph node and cultured in the presence of the antigenic peptide. $^3$H-thymidine uptake was then measured to determine the proliferation of T cells. Blood was collected after the immunization and the antigen-specific IgG antibodies were quantified with an enzyme-antibody method.

The invention will now be further described by the following numbered paragraphs:

1. A nonhuman animal model lacking the function to control lymphocyte migration wherein the function to control lymphocyte migration is lacked or suppressed by deleting DOCK2 gene on the chromosome.
2. The nonhuman animal model lacking the function to control lymphocyte migration according to paragraph 1, wherein the function to control lymphocyte migration is a function to mediate cytoskeletal reorganization through activating Rac.
3. The nonhuman animal model lacking the function to control lymphocyte migration according to paragraph 1, wherein the function to control lymphocyte migration is a migration function of lymphocytes in response to stimuli with chemokines such as SLC, SDF-1, BLC.
4. The nonhuman animal model lacking the function to control lymphocyte migration according to paragraph 1, wherein the function to control lymphocyte migration is a homing function to secondary lymphoid organs such as spleen, lymph nodes and Peyer's patches.
5. The nonhuman animal model lacking the function to control lymphocyte migration according to paragraph 1, wherein the function to control lymphocyte migration is a function to emigrate mature thymic T cells into peripheral blood in response to chemokine stimulus with ELC or a function of intra-thymus migration of $CD4^+CD8^+$ immature thymocytes in response to chemokine stimulus with SDF-1.
6. The nonhuman animal model lacking the function to control lymphocyte migration according to any of paragraphs 1 to 5, wherein actin polymerization in response to chemokine stimulus is almost totally disappeared in lymphocytes.
7. The nonhuman animal model lacking the function to control lymphocyte migration according to any of paragraphs 1 to 6, wherein marked atrophy of lymphoid follicles, straying of lymphocytes into red pulp, and disappearance of marginal-zone B cells are observed.
8. The nonhuman animal model lacking the function to control lymphocyte migration according to any of paragraphs 1 to 7, wherein the nonhuman animal is a mouse.
9. A method for screening a promoter or suppressor of the function to control lymphocyte migration, wherein a test substance is administered to the nonhuman animal model lacking the function to control lymphocyte migration according to any of paragraphs 1 to 8, or a test substance is brought into contact with tissues, organs or cells from said nonhuman animal model and a wild-type animal to measure/assess the change in the function to control lymphocyte migration.
10. The method for screening a promoter or suppressor of the function to control lymphocyte migration according to paragraph 9, wherein the change in the function to control lymphocyte migration is a change in the active GTP-bound Rac.
11. The method for screening a promoter or suppressor of the function to control lymphocyte migration according to paragraph 9, wherein the change in the function to control lymphocyte migration is a change in the migration activity of lymphocytes in response to stimuli with chemokines such as SLC, SDF-1, BLC, etc.
12. The method for screening a promoter or suppressor of the function to control lymphocyte migration according to paragraph 9, wherein the change in the function to control lymphocyte migration is a change in the homing activity to secondary lymphoid organs such as spleen, lymph nodes, Peyer's patches and the like.
13. The method for screening a promoter or suppressor of the function to control lymphocyte migration according to paragraph 9, wherein the change in the function to control lymphocyte migration is a change in the number of mature T cells in peripheral blood in response to chemokine stimulus with ELC, or a change in the intra-thymic migration activity of CD4+CD8+ immature thymocytes in response to chemokine stimulus with SDF-1.
14. The method for screening a promoter or suppressor of the function to control lymphocyte migration according to paragraph 9, wherein the change in the function to control lymphocyte migration is a change in the degree of actin polymerization in lymphocytes in response to chemokine stimuli.
15. The method for screening a promoter or suppressor of the function to control lymphocyte migration according to paragraph 9, wherein the change in the function to control lymphocyte migration is a change in the degrees of atrophy of lymphoid follicles, straying of lymphocytes into red pulp, and disappearance of marginal-zone B cells.
16. The method for screening a promoter or suppressor of the function to control lymphocyte migration according to any of paragraphs 9 to 15, wherein the test substance is a molecule which binds to DOCK2.
17. The method for screening a promoter or suppressor of the function to control lymphocyte migration according to any of paragraphs 9 to 16, wherein the degrees of change in the function to control lymphocyte migration of a nonhuman animal lacking DOCK2 gene on the chromosome and of a wild-type nonhuman animal are compared and assessed.
18. The method for screening a promoter or suppressor of the function to control lymphocyte migration according to any of paragraphs 9 to 17, wherein the nonhuman animal is a mouse.
19. A promoter or suppressor of the function to control lymphocyte migration obtained by the method for screening according to any of paragraphs 9 to 18.
20. The suppressor of the function to control lymphocyte migration according to paragraph 19, wherein said suppressor is an anti-DOCK2 antibody, a DOCK2-binding molecule or an antisense strand of DOCK2 gene.
21. A method for screening a therapeutic agent for immune-related diseases such as allergy, antoimmune diseases, GvH, graft rejections, wherein the method for screening a promoter or suppressor of the function to control lymphocyte migration according to any of paragraphs 9 to 18 is used.
22. A therapeutic agent for immune-related diseases such as allergy, autoimmune diseases, GvH, graft rejections obtained by the screening method according to paragraph 21.
23. The therapeutic agent for immune-related diseases according to paragraph 22, which is an anti-DOCK2 antibody, a DODK2-binding molecule or an antisense strand of DOCK2 gene.
24. A protein for controlling lymphocyte migration which mediates reorganization of cytoskeleton through activating Rac.
25. The protein for controlling lymphocyte migration according to paragraph 24, wherein said protein is DOCK2 and a DOCK2 variant.
26. The protein for controlling lymphocyte migration according to paragraph 25, wherein DOCK2 is an expression product of Hch gene (GenBank: accession No. AYO27438).
27. A method using the protein according to any of paragraphs 24 to 26 for controlling lymphocyte migration.
28. DNA encoding a protein for controlling lymphocyte migration which mediates reorganization of cytoskeleton through activating Rac.
29. DNA encoding the protein for controlling lymphocyte migration according to paragraph 28, wherein said DNA is DOCK2 gene and a DOCK2 gene variant.
30. DNA encoding the protein for controlling lymphocyte migration according to paragraph 29, wherein DOCK2 gene is Hch gene (GenBank: accession No. AYO27438).
31. A method using DNA according to any of paragraphs 28 to 30 for expressing the protein for controlling lymphocyte migration.

INDUSTRIAL APPLICABILITY

The present invention revealed that DOCK2, a haematopoietic cell-specific CDM family protein, is indispensable for lymphocyte chemotaxis. DOCK2-deficient mice (DOCK2$^{-/-}$) exhibited migration defects of T and B lymphocytes, but not of monocytes, in response to stimuli with chemokines, resulting in abnormalities including T lymphocytopenia, atrophy of lymphoid follicles and loss of marginal-zone B cells. In DOCK2$^{-/-}$ lymphocytes, chemokine-induced Rac activation and actin polymerization were almost totally disappeared. Thus, DOCK2 is shown to control lymphocyte migration by functioning as a main molecule that mediates cytoskeletal reorganization through Rac activation. For this reason, by using the animal model of the present invention, immune-related diseases such as allergy, autoimmune diseases, GvH and graft rejection, or the pathogenic conditions can be elucidated at a molecular level and a novel therapy for these diseases or pathogenic conditions can be developed by targeting

The invention claimed is:
1. A transgenic mouse whose genome comprises a homozygous deletion in the endogenous DOCK2 gene, wherein said homozygous deletion prevents the production of functional DOCK2 protein, wherein a function controlling lymphocyte migration in said transgenic mouse is suppressed.
2. The transgenic mouse of claim 1, wherein the function controlling lymphocyte migration is a function to mediate cytoskeletal reorganization through activating Rac.
3. The transgenic mouse of claim 1, wherein the function controlling lymphocyte migration is a migration function of lymphocytes in response to stimuli with a chemokine.
4. The transgenic mouse of claim 1, wherein the function controlling lymphocyte migration is a homing function to secondary lymphoid organ.
5. The transgenic mouse of claim 1, wherein the function controlling lymphocyte migration is a function to emigrate mature thymic T cells into peripheral blood in response to chemokine stimulus with EBI1-ligand chemokine (ELC) or a function of intra-thymus migration of CD4+CD8+ immature thymocytes in response to chemokine stimulus with stroma-derived factor (SDF)-1.
6. The transgenic mouse of claim 1, wherein actin polymerization in lymphocytes in response to chemokine stimulus is abolished.
7. The transgenic mouse of claim 1, wherein marked atrophy of lymphoid follicles, straying of lymphocytes into red pulp, and disappearance of marginal-zone B cells are observed.
8. The transgenic mouse of claim 3, wherein the chemokine is selected from group consisting of secondary lymphoid organ chemokine (SLC), SDF-1, B-lymphocyte chemoattractant (BLC).
9. The transgenic mouse of claim 4, wherein the secondary lymphoid organs is selected from the group consisting of spleen, lymph nodes and Peyer's patch.

* * * * *

UNITED STATES PATENT AND TRADEMARK OFFICE
CERTIFICATE OF CORRECTION

PATENT NO. : 7,312,373 B2
APPLICATION NO. : 10/886364
DATED : December 25, 2007
INVENTOR(S) : Yoshinori Fukui and Takehiko Sasazuki It is certified that error appears in the above-identified patent and that said Letters Patent is hereby corrected as shown below:

On The Title Page should read,

Item (73)   Assignee: Japan Science and Technology Agency, "Kawaguchi-shi" --Saitama-- (JP)

Col. 20, claim 8, line 61, should read,

The transgenic mouse of claim 3, wherein the chemokine is selected from group consisting of secondary lymphoid organ chemokine (SLC), SDF-1, --and-- B-lymphocyte chemoattractant (BLC).

Signed and Sealed this

Twenty-ninth Day of July, 2008

JON W. DUDAS
*Director of the United States Patent and Trademark Office*